(12) United States Patent
Ahluwalia et al.

(10) Patent No.: US 11,484,329 B2
(45) Date of Patent: Nov. 1, 2022

(54) SYSTEMS AND METHODS ASSOCIATED WITH ENDOSCOPIC SURGICAL INSTRUMENTS

(71) Applicants: Prabhat Kumar Ahluwalia, Little Falls, NY (US); Puja Ahluwalia, Little Falls, NY (US)

(72) Inventors: Prabhat Kumar Ahluwalia, Little Falls, NY (US); Puja Ahluwalia, Little Falls, NY (US)

( * ) Notice: Subject to any disclaimer, the term of this patent is extended or adjusted under 35 U.S.C. 154(b) by 302 days.

(21) Appl. No.: 16/517,613

(22) Filed: Jul. 21, 2019

(65) Prior Publication Data

US 2019/0336152 A1 Nov. 7, 2019

Related U.S. Application Data

(63) Continuation of application No. PCT/US2018/018043, filed on Feb. 13, 2018.

(60) Provisional application No. 62/458,046, filed on Feb. 13, 2017.

(51) Int. Cl.
  *A61B 17/221* (2006.01)
  *A61B 17/00* (2006.01)
  *A61B 17/34* (2006.01)

(52) U.S. Cl.
  CPC ...... *A61B 17/221* (2013.01); *A61B 17/00234* (2013.01); *A61B 17/3423* (2013.01); *A61B 2017/00287* (2013.01)

(58) Field of Classification Search
  CPC ............ A61B 17/00234; A61B 17/221; A61B 17/3423; A61B 2017/00287; A61B 2017/00557; A61B 2017/00592
  See application file for complete search history.

(56) References Cited

U.S. PATENT DOCUMENTS

| | | | | |
|---|---|---|---|---|
| 5,611,803 | A * | 3/1997 | Heaven | A61B 17/00234 606/110 |
| 2009/0182292 | A1* | 7/2009 | Egle | A61B 17/00234 604/327 |
| 2011/0184433 | A1* | 7/2011 | Parihar | A61B 17/00234 606/114 |
| 2011/0299799 | A1* | 12/2011 | Towe | A61B 17/00234 383/117 |
| 2014/0052018 | A1* | 2/2014 | Hawkins | A61B 17/42 600/562 |
| 2016/0262763 | A1* | 9/2016 | Shankarsetty | A61B 17/1285 |

* cited by examiner

*Primary Examiner* — Mohamed G Gabr
(74) *Attorney, Agent, or Firm* — Pierson IP, PLLC

(57) ABSTRACT

Embodiments disclose surgical instruments for retrieving excised tissue from a patient and, more particularly, to endoscopic surgical instruments such as pouches or retrieval bags for the removal of tissue through a small incision.

13 Claims, 17 Drawing Sheets

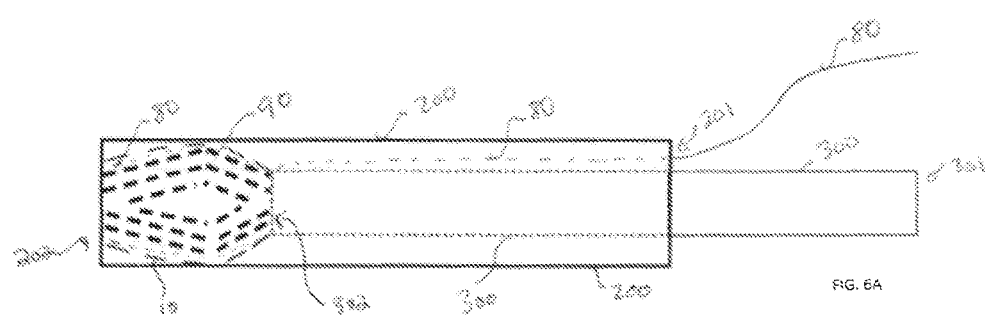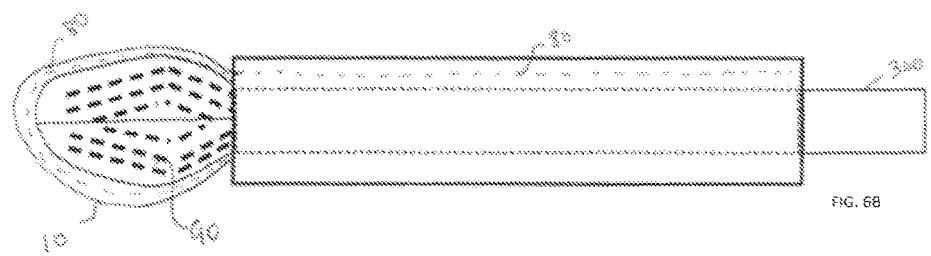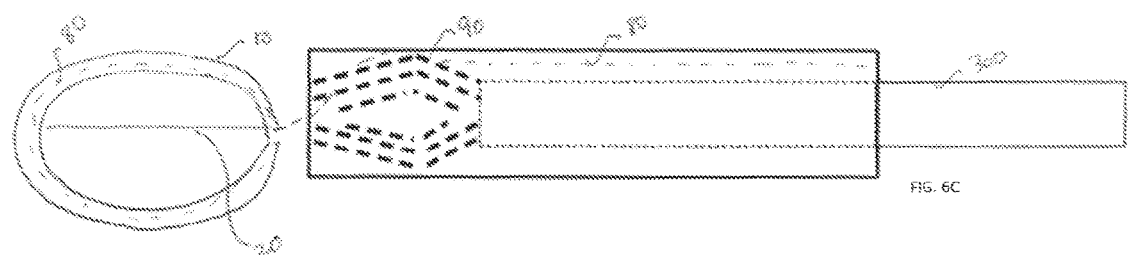

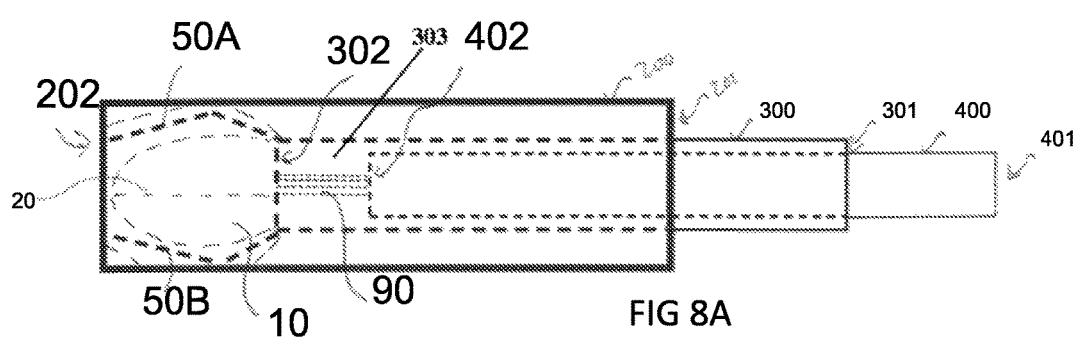
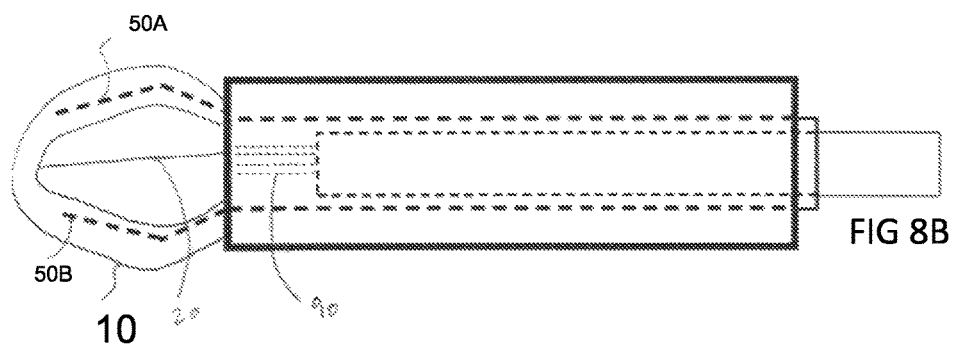

SYSTEMS AND METHODS ASSOCIATED WITH ENDOSCOPIC SURGICAL INSTRUMENTS

CROSS-REFERENCE TO RELATED APPLICATIONS

This application claims a benefit of priority under 35 U.S.C. § 119 to Provisional Application No. 62/458,046 filed on Feb. 13, 2017, which is hereby incorporated by reference in its entirety.

BACKGROUND INFORMATION

Field of the Disclosure

The present invention relates, in general, to surgical instruments for retrieving excised tissue from a patient and, more particularly, to endoscopic surgical instruments such as pouches or retrieval bags for the removal of tissue through a small or minimally invasive incision.

Background

Retrieval bags come in many standard configurations. Conventional retrieval bags are inserted into an abdominal cavity of a patient through a first incision. Typically retrieval bags are used with a grasping instrument inserted through a second incision, or trocar, that may grasp material, and place the material within the retrieval bag.

Conventionally, the retrieval bags have two opposing walls that are joined together to form a single wall. The joint wall forms a permanently bottom closed end 20, and a selectively opened top end 30 with a drawstring.

In use, a surgeon utilizes the grasping instrument to grasp a specimen and position the specimen within the opening of the conventional retrieval bag. The surgeon then closes the bag by manipulating the drawstring, and retrieves the bag through an abdominal incision.

However, while in use, the bag portion of conventional retrieval bag may remain compressed or closed, and difficult to open particularly at the bottom. The compression of the bag may lead to difficulties for the surgeon to position the material within the retrieval bag, and removing the retrieval bag through the first incision. This may require manipulation by a grasping instrument, which can lengthen operative time.

Accordingly, a need exists for easy and effective content and retrieval bags utilizing a guide-wire positioned within the retrieval bag, wherein the guidewire is configured to transition from a compressed mode to an expanded mode to increase the size of the bag.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

FIGS. 6A-6C show top-down views of an embodiments of a retrieval bag 10 coupled to a deployment or delivery instrument comprised of an introducer and actuator at various phases in deployment and withdrawal.

FIG. 8A-8E show top-down views of an embodiments of a retrieval bag 10 coupled to a deployment or delivery instrument comprised of an introducer, actuator and delivery rod at various phases in deployment and withdrawal.

DETAILED DESCRIPTION

In the following description, numerous specific details are set forth in order to provide a thorough understanding of the present embodiments. It will be apparent to one having ordinary skill in the art, that the specific detail need not be employed to practice the present embodiments. In other instances, well-known materials or methods have not been described in detail in order to avoid obscuring the present embodiments.

Figure 1A:
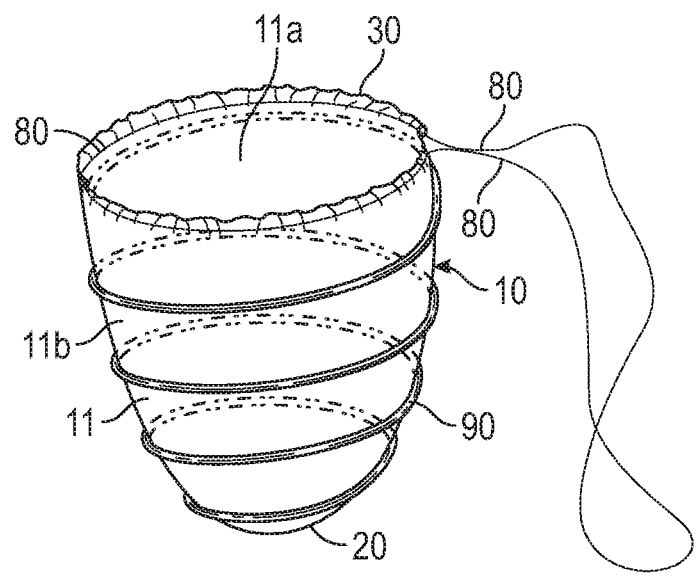
FIGS. 1A-1C show embodiments of a retrieval bag 10 in a resting state, partially compressed state and full compressed state, respectively.

FIG. 1A shows an embodiment of a retrieval bag 10, wherein one or more memory plastic, metal, or material, wires or guide-wires (hereinafter "memory wire 90") is coupled to a retrieval bag 10 and in first, expanded position. Retrieval bag 10 has two opposing walls 11a and 11b that when joined form a single wall, hereafter referred to as wall 11. The wall 11 is formed from at least one layer of a resilient or flexible material, and has a top open end 30 shown in the open position, and a bottom closed end 20. Wall 11 is tapered to facilitate removal of the retrieval bag 10 from the patient.

Memory wire is configured to collapse into a first compressed shape when receiving a compressive force, and expand into a second resting shape when the compressive force is released. Compression and release of memory wire 90 corresponds, respectively to compression and expansion of retrieval bag 10. Responsive to the one or more memory wires expanding, the retrieval bag expands. Responsive to the one or more memory wires collapsing, the retrieval bag collapses. Expansion of the memory wire 90 causes expansion of the retrieval bag 10 and minimizes or eliminates the need for the surgeon to manually open the retrieval bag with a grasper.

Figure 1B:
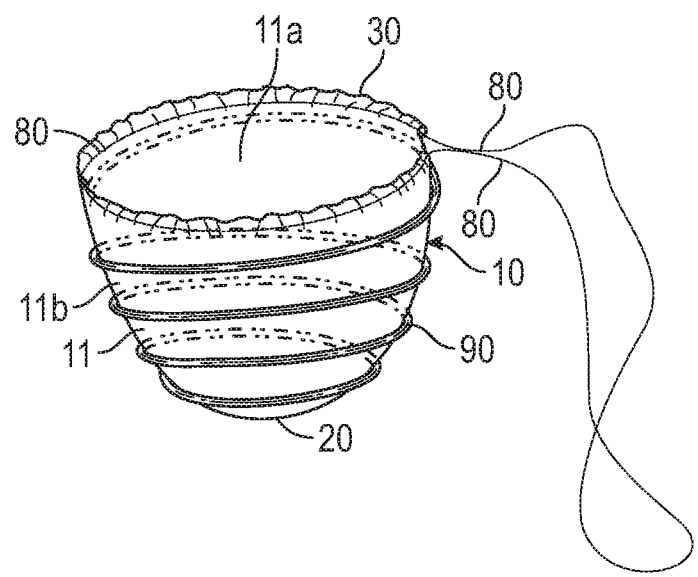
Figure 1C:
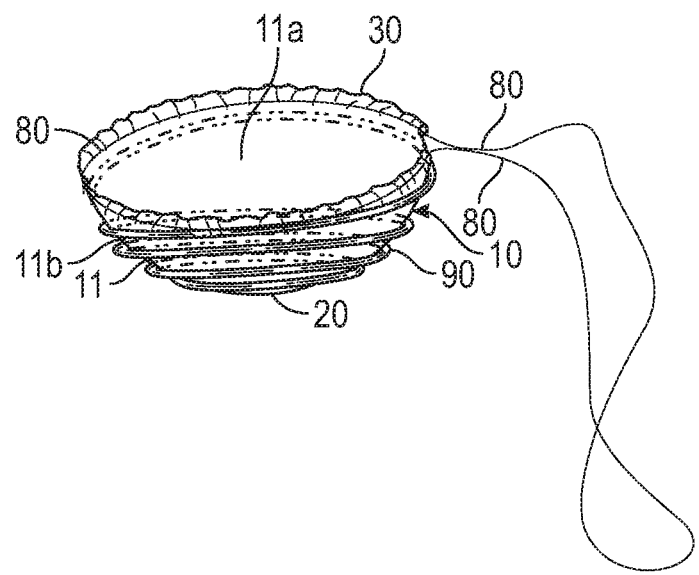

Memory wire 90 is configured to be in a first compressed state and a second expanded state. FIG. 1B shows an embodiment of a retrieval bag 10, wherein memory wire 90 is transitioning from an expanded position to a retracted position, or vice-versa. FIG. 1C shows an embodiment of a retrieval bag 10, wherein memory wire 90 is in a compressed position. Upon release of the compressive force in FIG. 1C, memory wire 90 expands open to end in a final resting state depicted in FIG. 1A.

Figure 3A:
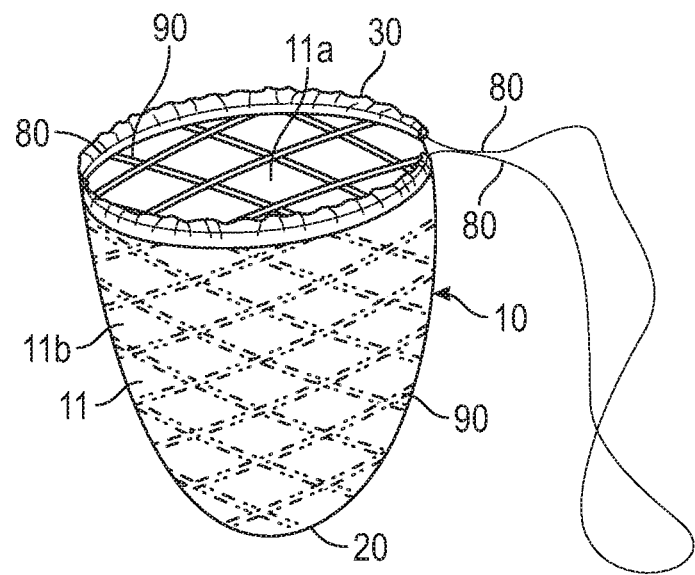
FIG. 3A shows an embodiment of a retrieval bag 10 with thatched memory wires.
Figure 3B:
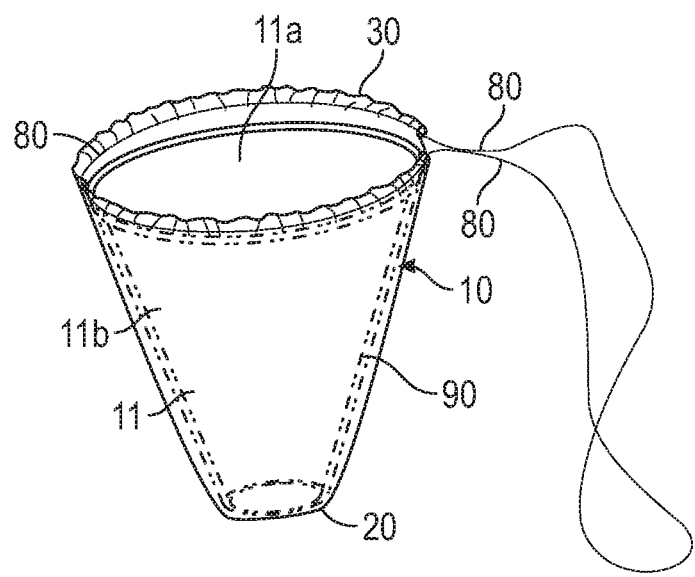
FIG. 3B shows an embodiment of a retrieval bag 10 with memory wire outlining the shape of the bag on the interior of the wall.
Figure 3C:
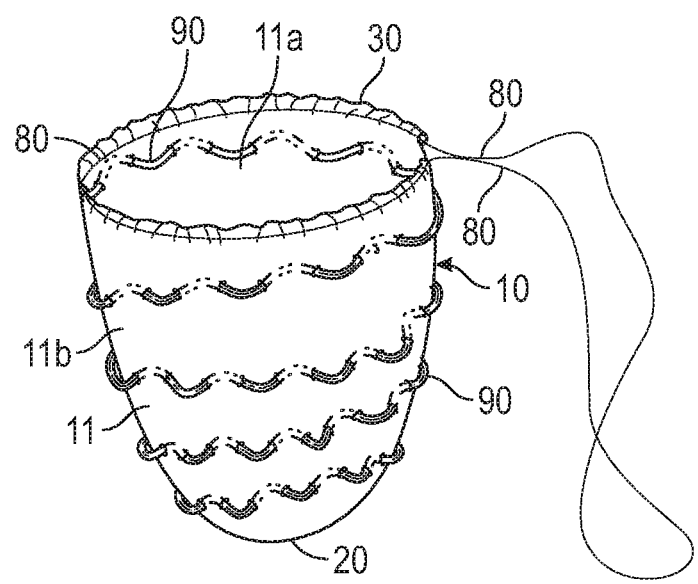
FIG. 3C shows an embodiment of a retrieval bag 10 wherein memory wire laces in and out of the bag's wall.
Figure 3D:
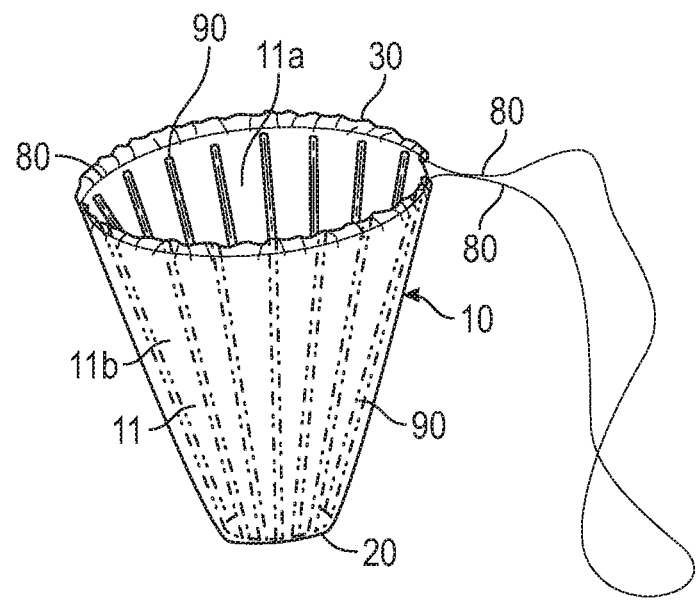
FIGS. 3D-3E show embodiments of a retrieval bag 10 wherein memory wires radiates in spokes.
Figure 3E:
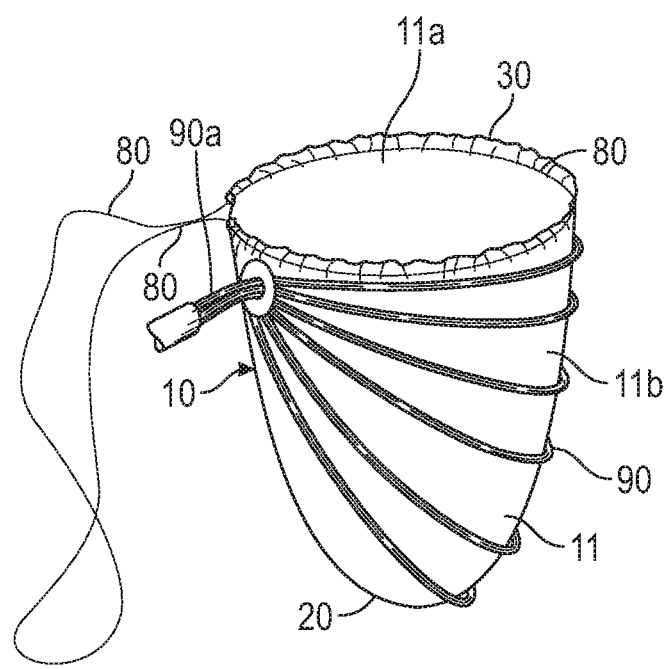
Figure 3F:
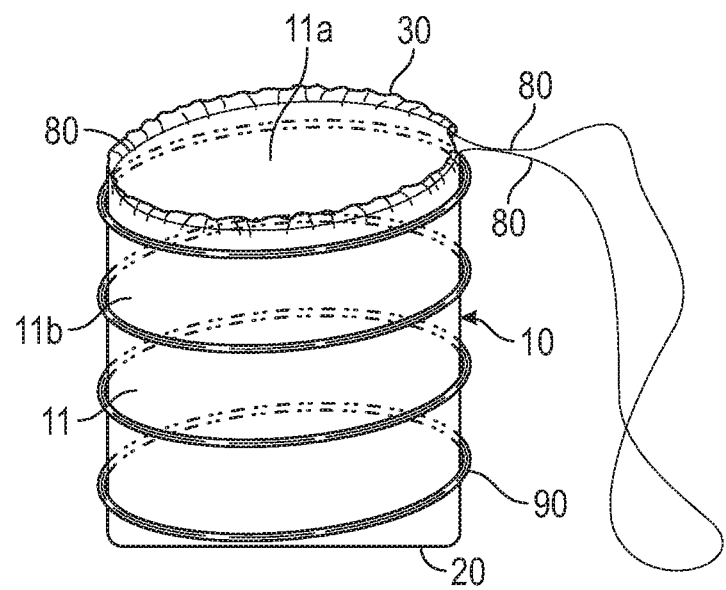
FIGS. 3F-3G shows embodiments of a retrieval bag 10 with alternative shapes of a square and oval, respectively.
Figure 3G:
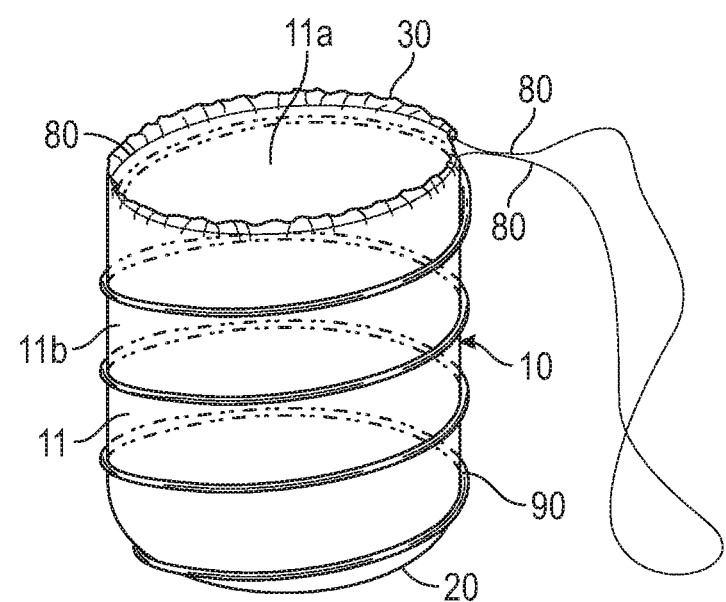

FIG. 1A shows an embodiment wherein memory wire 90 is on an outer surface 11b of wall 11. In this embodiment, memory wire 90 applies a pulling force to the exterior surface of retrieval bag 10 to expand retrieval bag 10, and a pushing force to the exterior surface of retrieval bag 10 to contract retrieval bag 10. This is also shown in FIGS. 3E, 3F, and 3G.

Figure 2A:
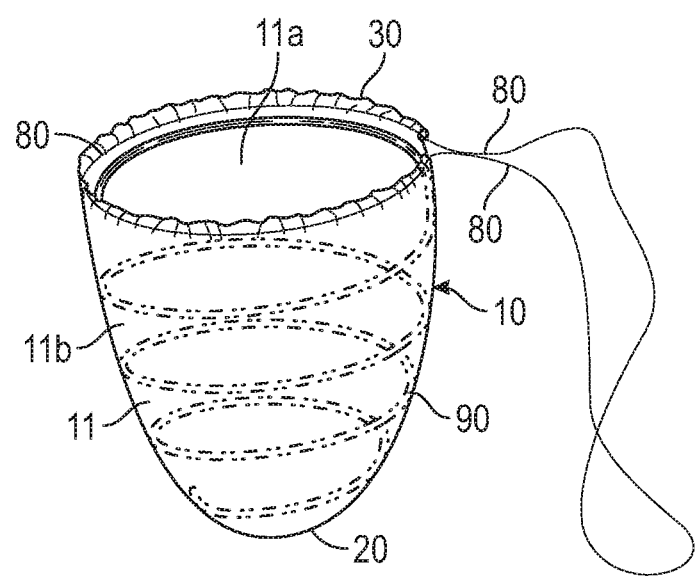
FIGS. 2A-2B show embodiments of a retrieval bag 10 with memory wire positioned on an inner bag wall and between bag walls, respectively.

FIG. 2A shows an embodiment wherein memory wire 90 is positioned on an inner surface of wall 11a. More specifically, memory wire 90 may sit in the interior of retrieval bag 10, wherein memory wire 90 applies a pushing force to the interior surface of retrieval bag 10 to expand retrieval bag 10, and a pulling force to the interior surface of retrieval bag 10 to contract retrieval bag 10. This is also shown in FIGS. 3A, 3B, and 3D.

Figure 2B:
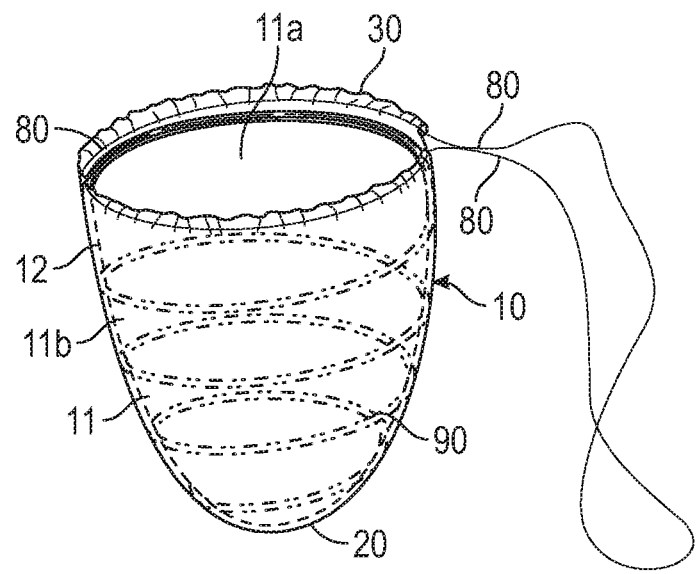

FIG. 2B shows an embodiment wherein memory wire 90 is positioned between one or more layers of walls, or more specifically wall 11 and wall 12. In other embodiments, memory wire 90 may lace in and out of one more wall layers, as shown in FIG. 3C.

Retrieval bag 10 expands conform to a shape of the expanded memory wire 90, wherein the shape of the expanded memory wire may be predetermined to a final resting state. Memory wire 90 may have any design or shape to facilitate expansion of the retrieval bag into unique designs and shapes upon deployment. The design characteristics of the turns of memory wire 90 may allow retrieval bag 10 to have different shapes based on surgical requirements.

A possible design or shape includes a spiral or spring shape, wherein memory wire 90 has equal diameters at every turn, narrowing in diameter at every turn (as shown in FIG. 2A), or expanding in diameter at every turn, respectively. Designs and shapes may be combined for unique configurations, such as an hourglass, which are both a spiral and a spring shape.

FIGS. 3A-3G show various possible designs and configurations of the memory wire 90 in relation to retrieval bag 10. In embodiments, memory wire 90 may be criss crossed, hatched (FIG. 3A), form a cup design (FIG. 3B), threaded design (FIG. 3C), have vertical or horizontal radiating spokes (FIGS. 3D & 3E). Memory wire 90 may be comprised of one or more unitary discrete pieces (FIGS. 3D & 3E) or be connected and continuous (FIGS. 3F & 3G) or any configuration of one or more pieces of memory wire that enables expansion of retrieval bag 10. Memory wire 90 may travel longitudinally and/or radially around the wall of the retrieval bag between the open end and the closed end, crossing other memory wires.

Retrieval bag 10 may form any shape, a regular or irregular, when expanded, and memory wire 90 may have a corresponding regular or irregular shape that facilitates the expansion of retrieval bag 10. For example, retrieval bag may form a square (FIG. 3F), oval (FIG. 3G), circle, or have regular or irregular curved walls 11, which may have angled, straight, or curved edges. Alternatively, retrieval bag may be triangular, trapezoidal or any other polygonal shape with angled edges to facilitate delivery and retrieval. In other embodiments, bag 10 may be combination of angled and curved edges.

Memory wire 90 may be coupled to retrieval bag 10 through various mechanisms including glue, straps, adhesives, heat welding, etc. Alternatively, memory wire 90 may be embedded within retrieval bag 10 through a series of holes within retrieval bag. Alternatively, memory wire 90 may be laced through retrieval bag 10 (FIG. 3C).

In embodiments, memory wire 90 may be comprised of any material that is configured to compress and elongate to a predetermined shape, or non-determined shape. For example, memory wire may be comprised of plastics, metals, composites, wires, nylon, nitinol, or polymeric or elastomeric materials, etc.

Wall 11 may be formed from any flexible material, including elastic or polymeric material such as Polyurethane, Polyethylene, Polypropylene, Silicone, Vinyl, Nylon, or Teflon, or any mesh materials. Multiple layer construction of the walls 11 are common and can incorporate flexible metal meshes, thermoformed plastic meshes, fabrics, or Kevlar for reinforcement. Walls 11 may be formed from flat sheets of Polyurethane or another flexible or elastomeric material and may be cut into a desired shape with sides 37 tapered as shown. Walls may be welded, attached or glued together.

Figure 4A:
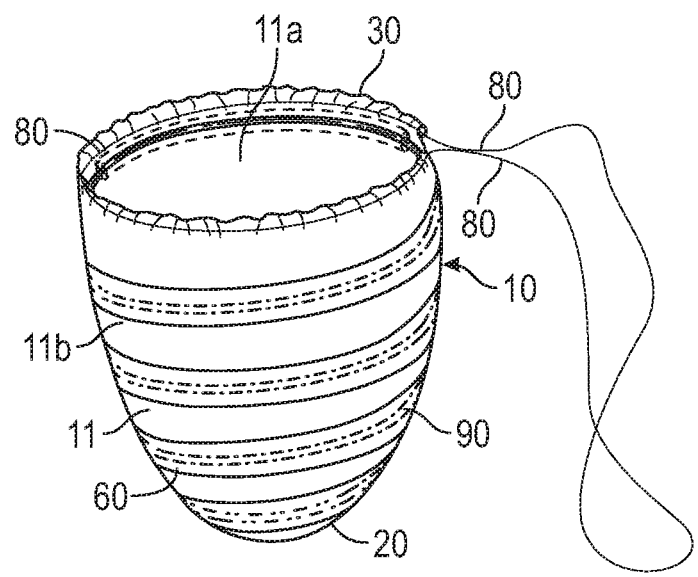
FIGS. 4A-4B shows an embodiment of a retrieval bag 10 with tunnels 60.
Figure 4B:
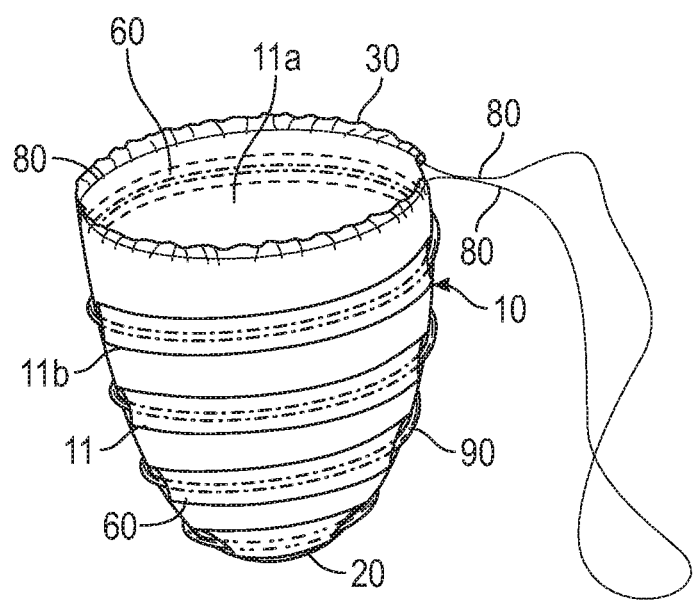

FIGS. 4A & 4B shows an embodiment of a retrieval bag 10 with a channel, tube or tunnel structure (hereinafter "tunnel 60") that facilitates passage of memory wire 90, houses memory wire 90, or couples memory wire 60 to retrieval bag 10. Tunnel 60 may comprised of any flexible material, including elastomeric or polymeric material such as Polyurethane, Polyethylene, Polypropylene, Silicone, Vinyl, Teflon, mesh materials, or any material suitable for coupling to the one or more interior or exterior wall(s) of retrieval bag 10. Multiple layer construction of the tunnels are possible and can incorporate flexible metal meshes, thermoformed plastic meshes, fabrics, or Kevlar for reinforcement. Tunnels may be formed from flat sheets of Polyurethane or another flexible or elastomeric material and may be cut into a desired shape. Tunnels may be welded, attached or glued together. Alternatively, tunnel 60 may be pre-formed with retrieval bag 10 or may be coupled to retrieval bag 10. The coupling may be by any method, including welding, gluing, heat-sealing, or stitching, etc. Tunnel 60 may also be formed by folding one or more layers of the retrieval bag 10 or wall 11.

Figure 5A:
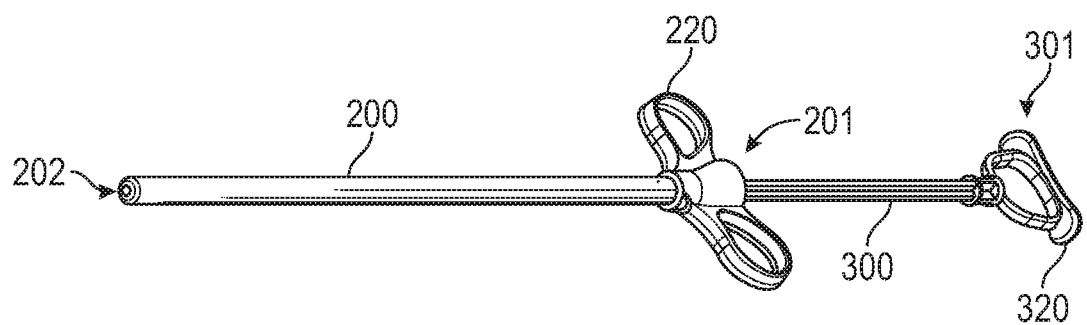
FIGS. 5A-5C show perspective views of an embodiment of a retrieval bag 10 coupled to a deployment or delivery instrument comprised of an introducer and actuator at various phases in a surgical procedure.
Figure 5B:
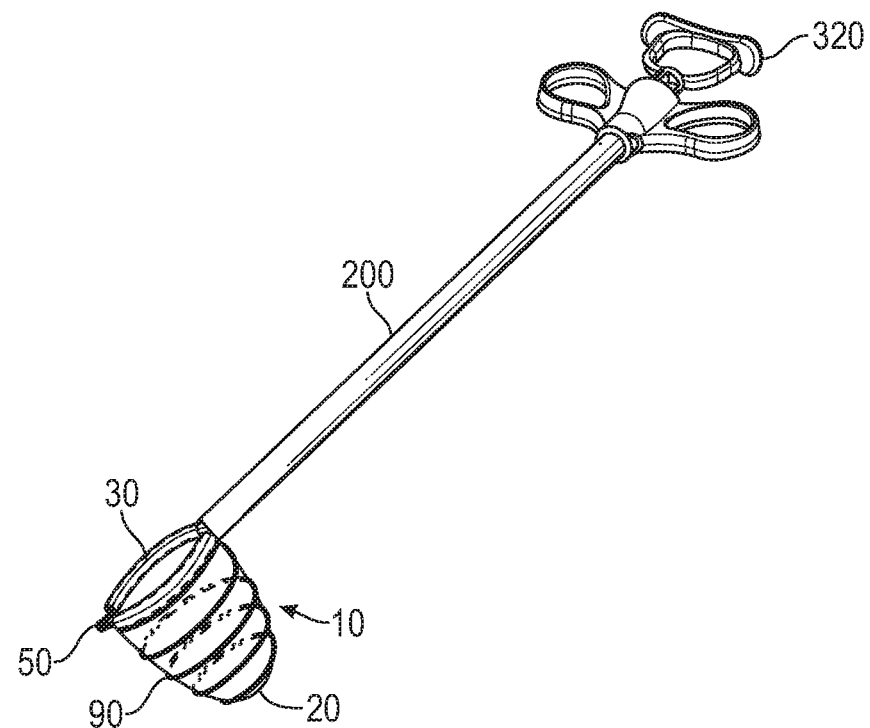

Tunnel 60 may have any design or shape that facilitates expansion of memory wire 90. FIGS. 5A & 5B shows a tunnel 60 positioned on exterior wall 11b with a spiral or spring shape configured to house a spiraling memory wire 90. In embodiments, this may be a regular spiral or spring shape with equal diameters at every turn, or narrowing in diameter, or expanding in diameter, depending on the desired resting shape of a retrieval bag.

Tunnel 60 may be designed to accommodate any shape or configuration of memory wire. Thus, like memory wire 90, tunnel 60 may also be hatched, crisscrossed, a cup design, a threaded design, or vertical or horizontal radiating spokes. Tunnel 60 may be one or more tunnels in discrete pieces or a single connected and continuous tunnel. Tunnel 60 may be any configuration that houses one or more pieces of memory wire 90 which enables expansion of the bag.

Tunnel 60 may be positioned on the interior wall of the retrieval bag 10, integrated with the retrieval bag 10, between layers of the bag (when there are multiple layers), or coupled to the exterior of retrieval bag 10.

Tunnel 60 may have any design or shape corresponding to memory wire 90. FIG. 4A shows an embodiment wherein tunnel 60 is a single continuous flow path for a single memory wire. Alternatively, FIG. 4B shows an embodiment wherein the tunnel 60 includes discreet paths with discreet memory wires. Specifically, memory wire 90 is comprised of discrete non-continuous pieces at intervals along the length of the retrieval bag 10. Similarly, the tunnel is comprised of discrete non-continuous tubes along the length of the retrieval bag 10 that house the memory wire.

Tunnel 60 may house memory wire 90, as shown in FIG. 4A. Alternatively, tunnel 60 may house only portions of memory wire 90 as shown in FIG. 4B, with portions of the memory wire exposed on the exterior surface of interior surface of retrieval bag 10.

Tunnel 60 and/or memory wire 90 may extend around retrieval bag 10, but may not reach the bottom, depending on the strength of memory wire. In embodiments, Tunnel 60 and/or memory wire 90 may travel ⅓, ⅔ or ½ the length of the bag.

Memory wire may be configured to enter and/or exit the tunnels depending on how retrieval bag 10 is deployed. To facilitate movement of memory wire 90 into and out of tunnel 60, memory wire 90 may have a softer proximal front end configured to enter the tunnel first and a harder firmer back distal end. Memory wire 90 may also be configured to have different diameters at different points. In some embodiments, the proximal end of the memory wire 90 configured for first entry into the tunnel may be smaller in diameter than the distal end of memory wire that travels the least amount of distance through tunnel 60. In embodiments where the tunnel is long (e.g., a spiral embodiment as in FIG. 5B), the memory wire 60's smaller diameter proximal end may be positioned closer to the retrieval bag's closed end and the larger diameter distal end maybe positioned closer to the retrieval bag's open end. This facilitates entry and exit of the memory wire 90 into tunnel 60 as the smaller diameter proximal end enables the memory wire to enter smoothly. The increasing larger diameter at the distal end provides structural support and strength to facilitate expansion of the retrieval bag to its desired open shape. The smaller diameter end configured for entering the tunnel first may also have a blunted end, knob or ball of material to minimize the risk of puncturing the bag.

In other embodiments, memory wire 90 may have smaller diameters at either end of each piece of memory wire and a larger diameter in the middle portion. This might be particularly advantageous in embodiments wherein only the end points of the memory are positioned in tunnels or tunnel pockets.

Figure 5C:
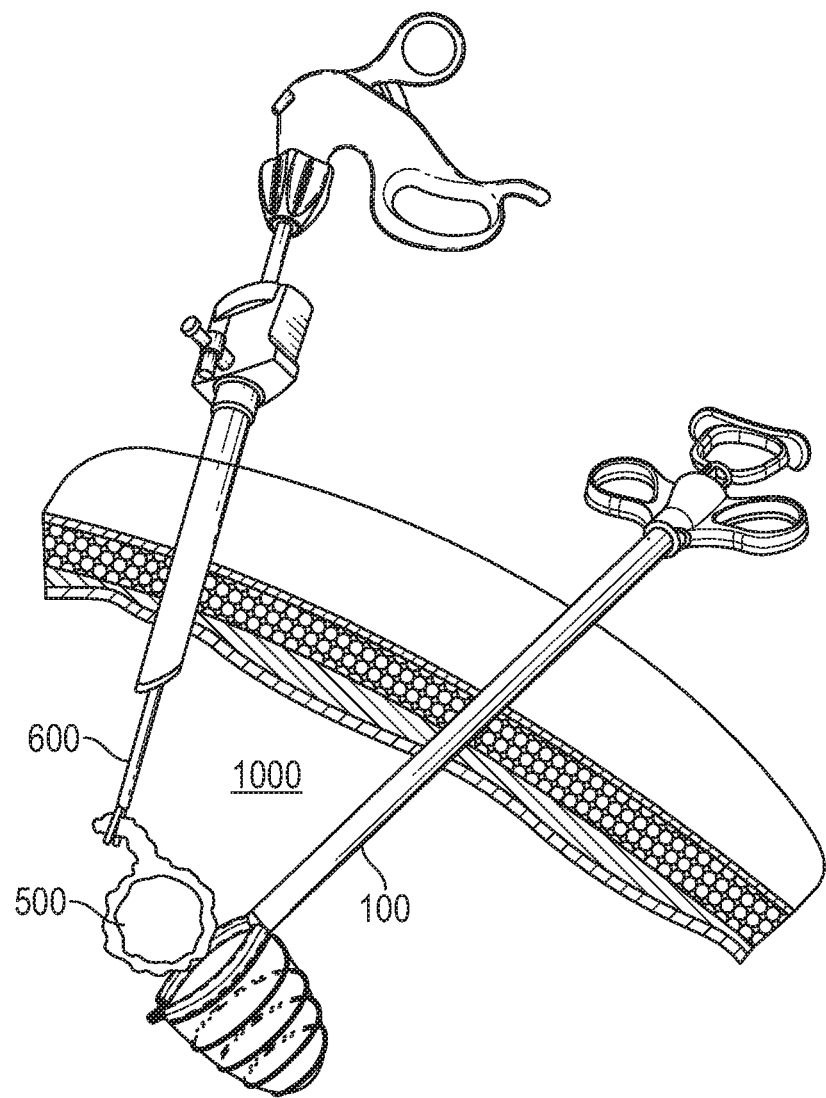

As shown in FIGS. 1-4, in embodiments, retrieval bag 10 may be configured to receive a drawstring, string, or cord (hereinafter "string 80") to facilitate closing retrieval bag 10 after a specimen has been placed inside. String 80 may be positioned on or adjacent to open end 30. String 80 may laced through bag 10 or, as shown in FIG. 5C, threaded into one or more channels 70 or tunnels 60 positioned along each side of open end 30 or surrounding open end 30. Responsive to an upward tensile force F, the string may close the bag and enable retrieval of retrieval bag 10 through an incision on the abdominal wall. String 80 may optionally include guide bead to provides and facilitate withdrawal of the bag, manipulation of the bag and opening/re-opening and closing/re-closing of the bag.

When retrieval bag 10 is inside of patient during a surgical procedure, for example in the peritoneal cavity, string 80 may extend from the retrieval bag 10 in the peritoneal cavity through a passageway (e.g., trocar) or through an incision in the patient to outside of the patient to facilitate retrieval.

Alternatively, retrieval bag 10 may be used in conjunction with a deployment instrument to facilitate retrieval. All of the embodiments of the retrieval bag herein described apply to the various embodiments of deployment instruments described below.

In the embodiments described herein of retrieval bag 10, memory wire 90 may be substituted by tunnels 60, wherein tunnels 60 are configured for receiving liquid or gas. This embodiment also enables expansion of the retrieval bag 10 to a predetermined shape without use of memory wire. In such embodiments, one or more tunnels are coupled to the retrieval bag and configured to expand upon injection of a fluid or gas and compress upon withdrawal of fluid or gas. Responsive to the one or more tunnels expanding, the retrieval bag expands; and wherein responsive to the one or more tunnels collapsing, the retrieval bag collapses. Retrieval bag 10 may be coupled to a luer lock to retain or release fluid within tunnels 60. The possible configurations of the fluid tunnels 60 relative to the retrieval bag 10 are the same as the previously described possible configurations of memory wire to the retrieval bag 10, as illustrated in FIG. 1-4.

Retrieval bags 10 may include a deployment instrument 100 to facilitate compression, delivery, expansion, and/or retrieval of the memory wire 90 and/or retrieval bag 10. Memory wire 90 may be in a compressed state by virtue of portions of memory wire 90 being positioned inside of deployment instrument 100. Responsive to memory wire 90 being positioned outside of deployment instrument 100, the compressive forces against memory wire 90 is no longer present. This allows memory wire 90 to expand into a larger volume. When coupled to retrieval bag 10, as memory wire 90 expands, retrieval bag 10 may correspondingly expand.

Depending on the attachment of memory wire 90 to retrieval bag 10, memory wire 90 may expand automatically and simultaneously when retrieval bag 10 exits a deployment instrument 100. In embodiments, the memory wire 90 is integrated into the bag 10 and compressed within the deployment instrument 100 before deployment. In particular, memory wire 90 may be positioned within tunnel 60, within the bag 10, and within deployment instrument 100 pre-deployment.

Alternatively, memory wire 90 may expand after the retrieval bag 10 is positioned outside of deployment instrument 100. The memory wire may be housed in the deployment instrument 100 and advanced into retrieval bag 10 after deployment of the retrieval bag 10 from the deployment instrument 100. In other embodiments, the memory wire may be partially positioned within the bag, but then advanced into the bag upon deployment from the deployment instrument 100.

FIGS. 5A-5C show an embodiment of a deployment instrument 100 comprised of an introducer 200 and an actuator 300. To illustrate the relationships in greater detail, FIGS. 6A-6C show a top down view of a simplified version.

The embodiment in FIGS. 6A-6C is not drawn to scale, but merely serve illustrative purpose in showing the relationships between various components.

As shown in FIG. 5A, introducer 200 is a hollow lumen with a handle assembly 220 extending on the proximal end. The handle assembly has a pair of finger loops or grips utilized to hold or stabilize the introducer. The introducer's proximal end 201 and the distal end 202 are open. Handle 320 is positioned on the actuator's proximal end 301 to control or facilitate movement of the actuator 300 relative to the introducer 200.

FIGS. 5A & 6A show an embodiment in a first compressed position wherein the actuator's distal end 302 is positioned proximal to the introducer's distal end 202. Actuator's distal end 302 is coupled to memory wire 90, which in turn is coupled to the compressed retrieval bag 10. Retrieval bag 10 is compressed in the introducer's distal end 202. In embodiments with tunnels 60, memory wire 90 may be pre-positioned within the tunnels of retrieval bag 10.

FIGS. 5B & 6B shows an embodiment in a second deployed position. After applying a compressive force upon actuator 300, actuator's distal end 302 is pushed towards the introducer's distal end 202, deploying retrieval bag 10 and memory wire 90 out from the introducer's distal end 202 and into the body cavity. Once deployed into the body cavity, the retrieval bag 10 is suspended and held open by memory wire 90. The memory wire 90 extends radially and longitudinally to open the bottom closed end as well as the top open end. In this step, flexible arms 50a and 50b extending from the distal end of the actuator coupled to the retrieval bag's opening may further facilitate opening the bag, though this is optional.

Figure 5D:
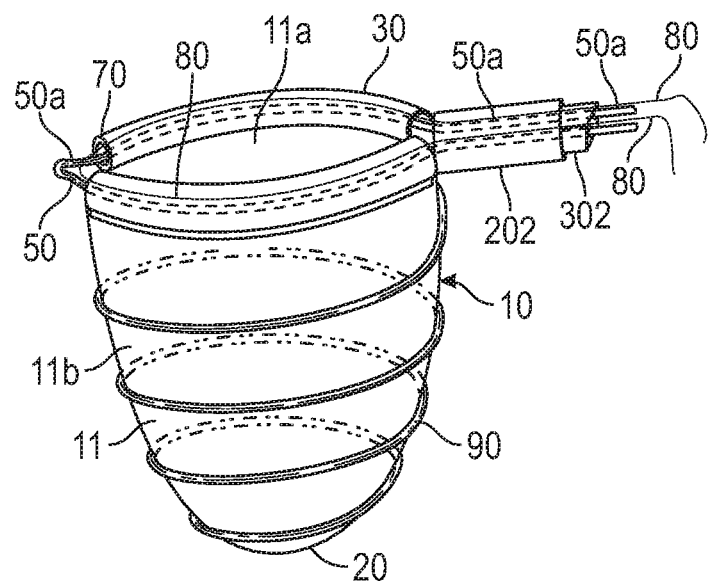
FIGS. 5D-5E show an embodiment of a retrieval bag 10 configured for coupling to a deployment instrument comprised of an introducer and actuator.
Figure 5E:
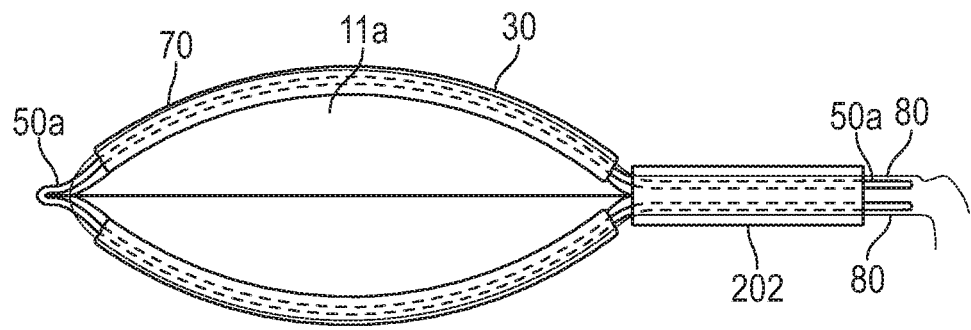

FIGS. 5D and 5E respectively show a perspective and top down view of flexible arms 50a and 50b with respect to bag 10. Flexible arms 50a and 50b are respectively coupled to the actuator's distal end 302, and extend through the introducer's distal end 202 to deploy retrieval bag 10 into the cavity. Flexible arms 50a and 50b is an optional feature in embodiments.

As shown in FIG. 5C, after deployment, specimens 500 may be collected via a grasper 600 and deposited into retrieval bag 10 in the body cavity 1000. After the retrieval bag 10 is filled, a surgeon may withdraw deployment instrument 100 with the specimen.

Withdrawal is accomplished by first applying a retractive pull or tensile force to the actuator 300, whereby the actuator 300 is withdrawn from the introducer's first distal end 202 towards the introducer's first proximal end 201. Pulling the actuator decouples and withdraws the memory wire 90 from retrieval bag 10 from the introducer's distal end 202 towards the introducer's proximal end 201, as shown in FIG. 6C. As a result, retrieval bag 10 collapses from it's expanded memory wire shape and is ready for withdrawal from a minimally invasive incision.

The embodiments described herein and in FIGS. 5 & 6 may be further improved by including one or more tunnel(s) 90 configured for receiving fluid or gas (hereinafter "fluid"). In embodiments, the actuator's longitudinal body may be lumen with a hollow inner channel 303 in fluid communication with tunnels 60. Actuator 300 may have a fluid intake port 350 at its proximal end 301. The intake port 350 may be a luer lock. Upon delivery of fluid into the actuator's intake port 350, fluid travels through hollow inner channel 303 and into tunnels 60 of retrieval bag 10. Thus, the actuator may deliver fluid into the one or more tunnels.

Attaching a syringe with fluid or gas to the actuator's intake port 350 and pushing the syringe piston towards the syringe's distal end may accomplish delivery of fluid. Fluid may be withdrawn from the tunnels by pulling the syringe piston towards the syringe's proximal end. A delivery rod 400 may be employed to facilitate pushing the fluid through the actuator's hollow inner channel 303, in addition or in lieu of a syringe. This embodiment may be advantageous for scenarios wherein the memory wire does not provide sufficient strength, or in lieu of a memory wire.

Figure 7A:
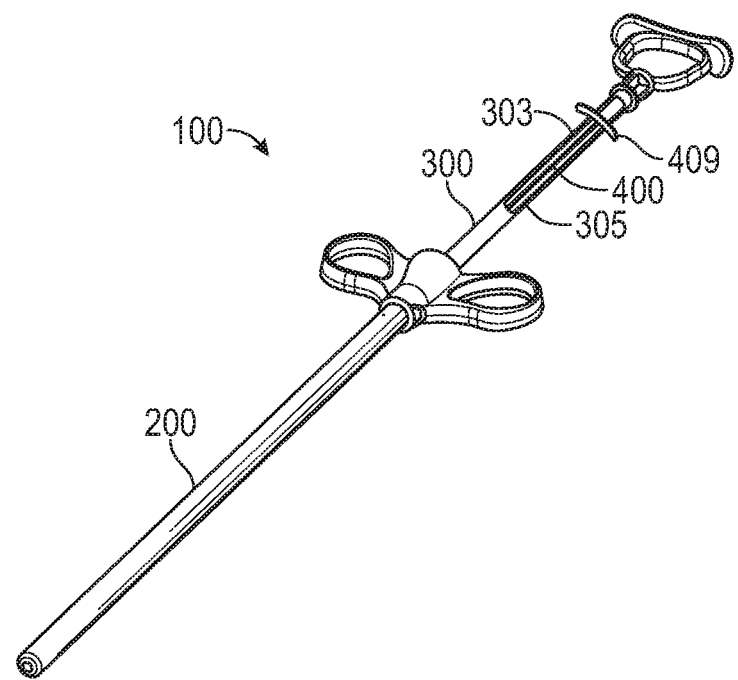
FIGS. 7A-7C show perspective views of an embodiment of a retrieval bag 10 coupled to a deployment or delivery instrument comprised of an introducer, actuator and delivery rod at various phases in a surgical procedure.
Figure 7B:
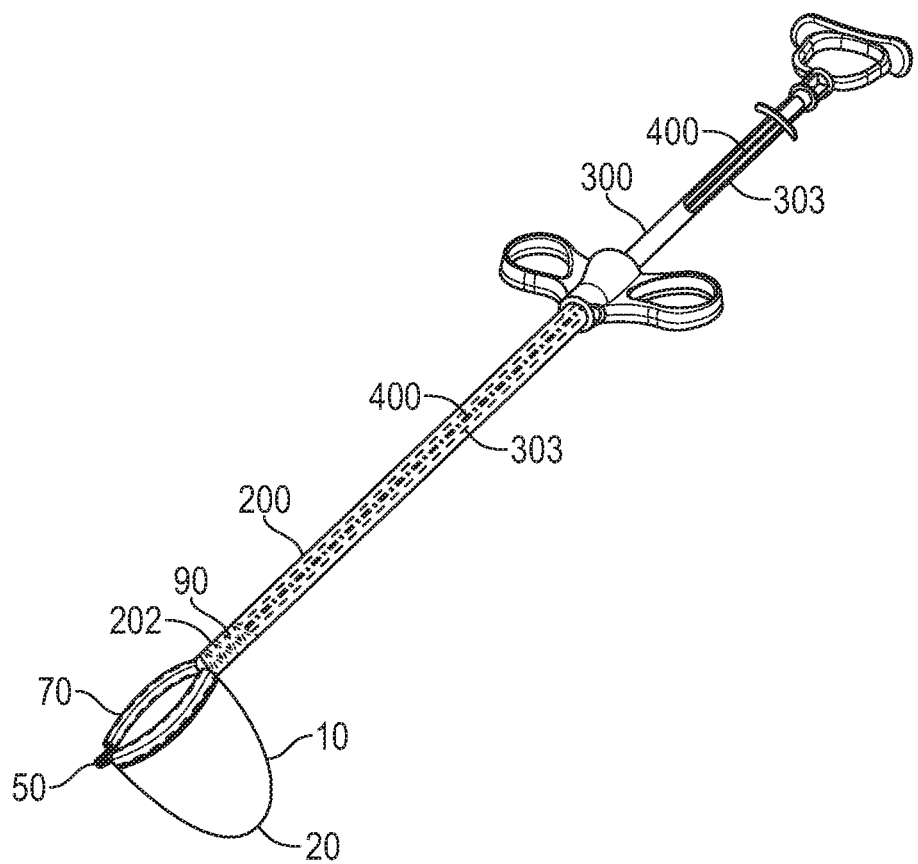
Figure 7C:
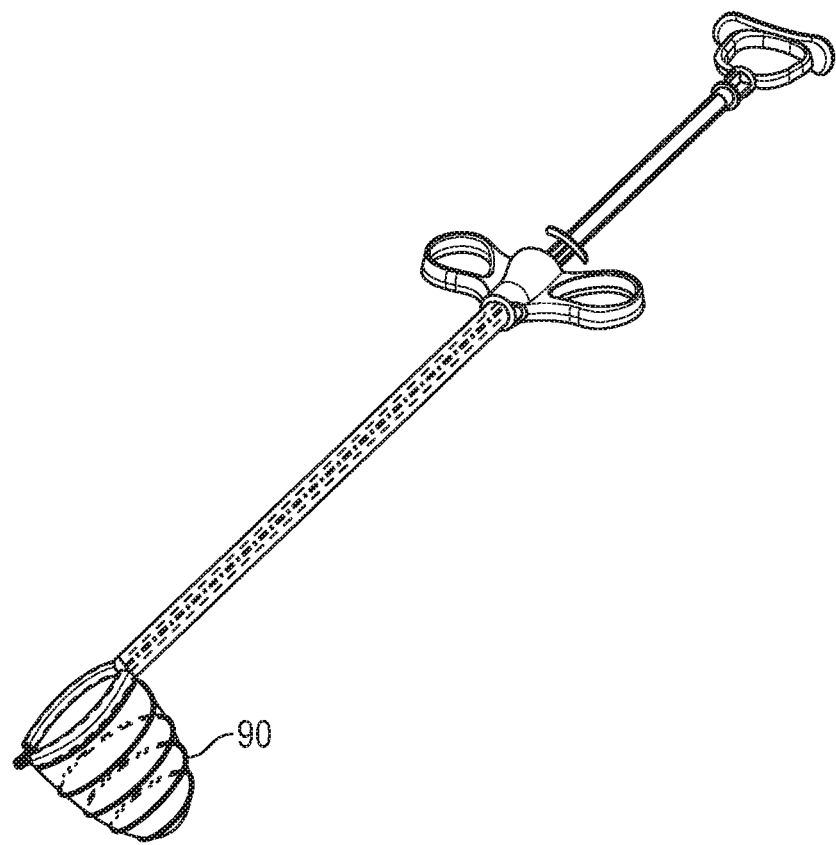
Figure 8C:
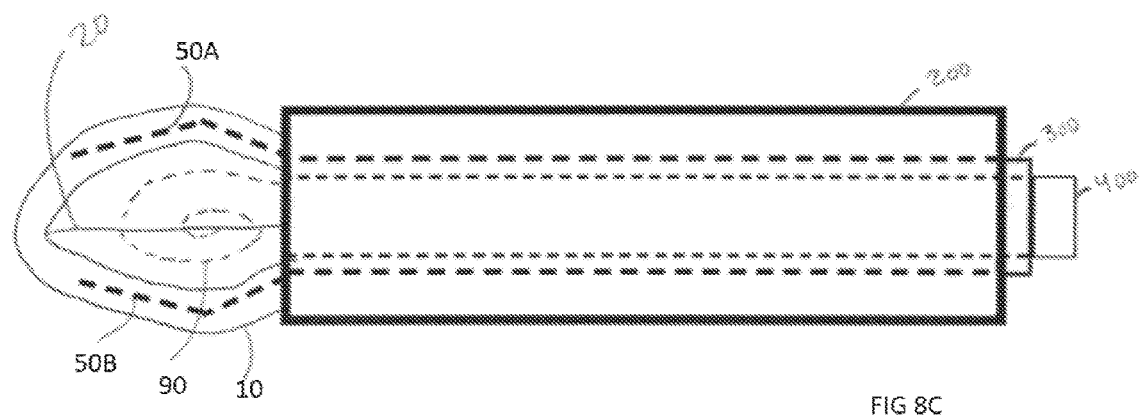

The embodiment shown in FIGS. 5 & 6 may be further improved upon to include a delivery rod 400, as shown in FIGS. 7A-7C and FIGS. 8A-8E. In these embodiments, actuator 300 further includes a hollow inner channel 303 in fluid communication with the actuator's distal end 302 and housing delivery rod 400. The embodiment in FIGS. 8A-8E are not drawn to scale, but merely serve illustrative purpose in showing the relationships between various components. FIGS. 7A & 8A show a first compressed position, wherein the introducer's proximal end 201 is distal to the actuator's proximal end 301. The retrieval bag is positioned between the introducer's distal end 202 and the actuator's distal end 302. Retrieval bag 10 is coupled to flexible arms 50a and 50b, which extend from the distal end of the actuator 300 and couple to the retrieval bag 10. Memory wire 90 is housed in the distal end 302 of actuator's hollow inner channel 303 and is coupled to the delivery rod's distal end 402.

In the first compressed position, FIG. 8A shows an embodiment wherein the actuator's proximal end 301 is distal to the delivery rod's proximal end 401, whereas FIG. 7A shows an embodiment wherein the actuator's proximal end 301 is not distal to the delivery rod's proximal end 401. FIG. 7A's embodiment includes an opening 305 at the proximal end of the actuator 300 with a button, slider, or grip (hereinafter grip 409") coupled to delivery rod. In FIG. 7A, grip 409 may be positioned along the longitudinal axis to achieve the desired translation of the delivery rod 400 with respect to the actuator 300. In FIG. 8A, delivery rod 400 may simply be pushed into the actuator 300 to achieve translation. The embodiment illustrated in FIG. 7A helps reduce the device length required for achieving translation of the delivery rod 400 with respect to the actuator 300.

In the embodiments of FIGS. 7 and 8, deployment is achieved in two steps. As shown in FIGS. 7B & 8B, in the first deployment step, actuator 300 is pushed into introducer 200. Upon this compressive force to the actuator, flexible arms 50a and 50b coupled to the distal end of the actuator 300 extend out of the introducer's distal end opening 202 into channels 70 on retrieval bag 10, deploying the attached retrieval bag 20 and opening retrieval bag's open end 30. Memory wire 90 however remains housed within the actuator's hollow inner channel 303, proximal to the deployed retrieval bag 10 and flexible arms 50, and distal to delivery rod 400 housed within actuator inner channel 303.

In the second step, as shown in FIGS. 7C & 8C, delivery rod 400 is pushed towards the introducer 200. Upon this compressive force to delivery rod 400, memory wire 90 is delivered from the actuator's distal end 302 into the deployed retrieval bag 10 so as to expand the retrieval bag.

After deployment, specimens may be collected via a grasper and deposited into retrieval bag 10. After the retrieval bag 10 is filled, a surgeon may withdraw deployment instrument 100 with the specimen.

Figure 8D:
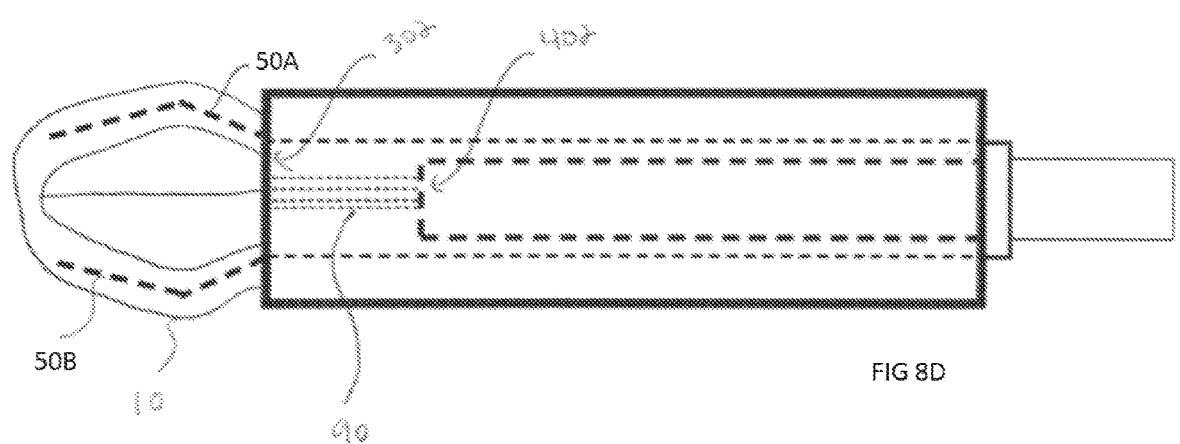

Referring to FIG. 8D, withdrawal is accomplished in two steps. The first step is applying a retractive pull or tensile force to delivery rod 400, whereby delivery rod 400 is withdrawn from the actuator's distal end 302. Pulling delivery rod 400 decouples and withdraws the memory wire 90 from retrieval bag 10 and pulls memory wire 90 towards actuator's distal end 302. As a result, retrieval bag 10 loses the shape of the expanded memory wire. This allows the retrieval bag 10 to easily compress when removed from a port or incision on the patient.

Figure 8E:
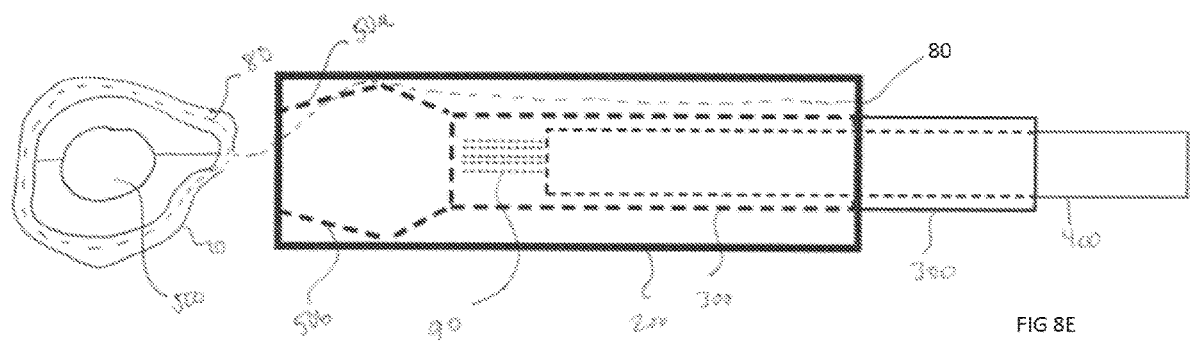

As shown in FIG. 8E, the second step is applying a retractive pull or tensile force to the actuator 300, whereby actuator 300 is withdrawn from the introducer's distal end 202 and pulled towards the introducer's proximal end 201. Pulling the actuator 300 decouples and withdraws the flexible arms 50a and 50b from retrieval bag into the introducer's proximal end 202. As a result, retrieval bag's open end 30 collapses. This allows the retrieval bag 10 to lose its shape from the expanded memory wire 90 and easily compress when removed from a port or incision on the patient. A string 80 may be coupled to retrieval bag 80 and extend through the introducer's lumen or actuator's lumen to facilitate retrieval of the bag after the deployment instrument 100 has been withdrawn from the patient.

Figure 9A:
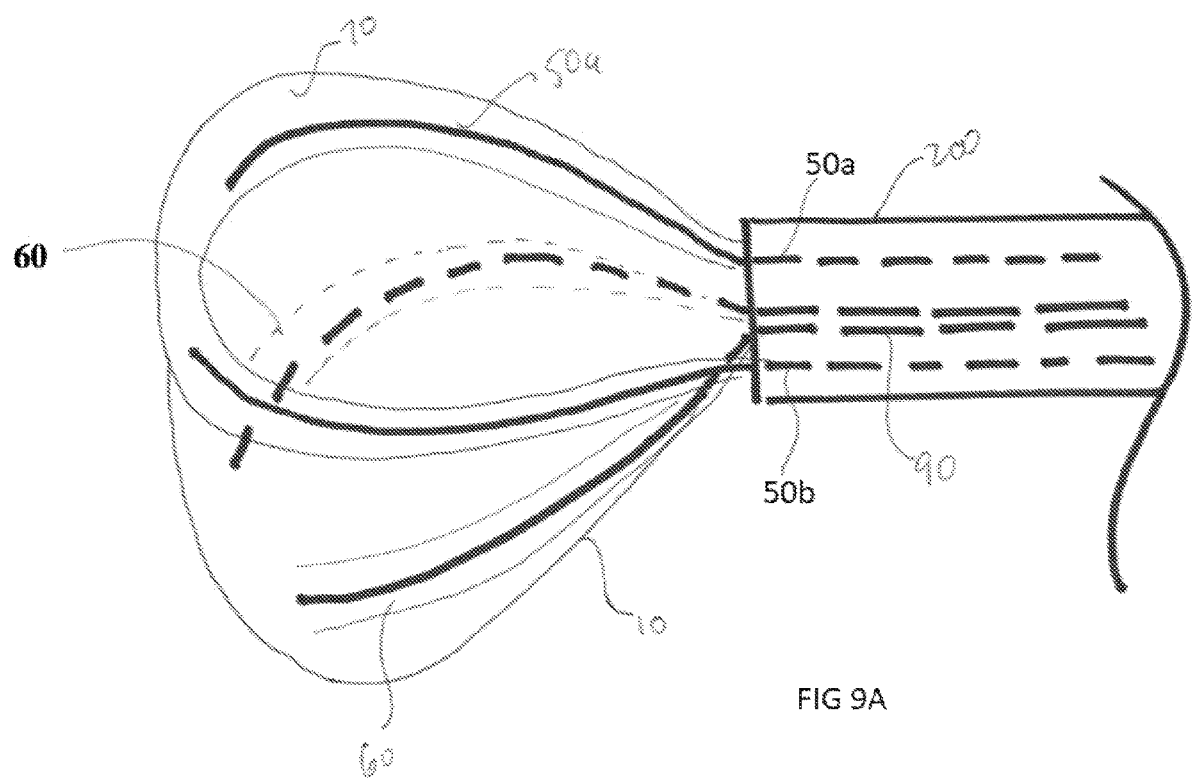
FIG. 9A shows an embodiment of a retrieval bag 10 with flexible arms and memory wire.

The embodiments described herein may be further improved by including one or more tunnel(s) 60 configured for receiving fluid or gas (hereinafter "fluid"). In embodiments, the delivery rod 400 may be lumen with a hollow inner channel 405 in fluid communication with tunnels 60. FIG. 9A shows an embodiment wherein tunnels 60 facilitate guidance of the memory wire 90 and are in fluid communication with delivery rod 400. Delivery rod 400 may have a fluid intake port 450 at its proximal end 401. The intake port 450 may be a luer lock. Upon delivery of fluid into the delivery rod's intake port 450, the fluid travels through hollow inner channel 405 and into tunnels 60 of retrieval bag 10. Delivery rod 400 may deliver fluid into the one or more tunnels 60.

Delivery of fluid may be accomplished by attaching a syringe with fluid or gas to the actuator's intake port 350 and pushing the syringe piston towards the syringe's distal end. Fluid may be withdrawn from the tunnels by pulling the syringe piston towards the syringe's proximal end. This embodiment may be advantageous for scenarios wherein the memory wire does not provide sufficient strength, or in lieu of a memory wire.

In the described embodiments, memory wire 90 may exit the introducer's distal end 202 or actuator's distal end 302 in various ways to facilitate expansion of the retrieval bag 10. For example, it may exit as a single continuous spiral as shown in FIG. 5B, a spoked array fashion as shown in FIG. 3E, or any embodiment described herein. Memory wire 90 may be advanced inside the retrieval bag 10, outside the bag, between layers of the retrieval bag 10, through layers of the retrieval bag 10, or through one or more tunnels 60 of the retrieval bag 10 to achieve expansion of the bag, as described previously. FIG. 9A shows an embodiment wherein Tunnels 60 facilitate guidance of the memory wire 90.

The embodiments described herein may be further improved by including a string 80 positioned on the bag's open end. String 80 enables a surgeon to close the bag after retraction of the memory wire and/or flexible arms from the delivery bag 10, but before withdrawal from the patient by applying a tensile force with a grasper. In embodiments, such as the embodiment shown FIGS. 6A-6C and FIGS. 8A-8E, String 80 may extend through the lumen of the introducer 200 and either hang freely outside of the introducer's proximal end 201 and/or be attached to a portion of the actuator 300. After closing the drawstring, the surgeon may pull the string extending out of the introducer 200 to pull the retrieval bag 10 through the introducer 200 or, alternatively, pull the introducer 200 and bag 10 (hanging by the string 80) through an incision.

String 80 may be positioned in various way with a deployment instrument 100. In embodiments, String 80 may extend through the actuator's lumen and hang freely outside of the actuator 300, or extend through a free space between the introducer's lumen and the actuator's lumen and extends outside of the introducer 200. In other embodiments, string 80 may extend along the length of the actuator's lumen and extend outside of the actuator's slit 305 or outside of the actuator's proximal end 301. In embodiments with a delivery rod 400, String 80 may extend through a hollow inner channel of the delivery rod 400 and outside of the delivery rod's proximal end 401.

In embodiments described herein, flexible arms 50a and 50b may be attached to or integrated with the actuator 300 and may travel through channels 70 positioned along each side of the opening 30 or surrounding opening 30 of retrieval bag 10. As shown in FIG. 9A, channels 70 may slidably receive flexible arms 50 extending from the actuator's distal end 302. Flexible arms 50 assist memory wire 90 in opening retrieval bag 10 into the patient, or may be memory wire. Actuator 300 may be retracted proximally to withdraw the flexible arms 50a and 50b from the retrieval bag 10.

Other embodiments, however, may lack flexible arms 50a and 50b, or may only include one arm, particularly when the memory wire 90 is sufficient strength to open the bag. This is particularly true for the embodiment described in FIGS. 5 & 6, wherein the memory wire 90 is deployed from the actuator's distal end 302. The flexible arms 50 may be rendered moot and unnecessary for opening a bag when substituted by memory wire 90. Thus, while embodiments depicted show flexible arms 50, this feature is optional.

The embodiments described herein may have slight variations in features, placement and deployment. For example, the components of retrieval bag 10, flexible arms 50, and the memory wire 90 may be compressed separately to together so that they are released sequentially or simultaneously. Alternatively, some components may be combined or compressed together, while other are not.

Alternatively, embodiments may further include any necessary channels for housing components. For examples, in other embodiments, delivery rod 400 has a hollow inner channel for housing memory wire 90 or string 80, or alternatively for delivering fluid into tunnels 60.

Embodiments may have further various variations, some with challenges. In some embodiments, all of the components (introducer 200, actuator 300, retrieval bag 10) are retrieved at once. In other embodiments, memory wire 90 may remain coupled to retrieval bag 10 during withdrawal of the retrieval bag from patient. However, these embodiments lead to difficult withdrawal as the surgeon must withdraw the larger expanded volume, not collapsed, retrieval bag 100 through a port or incision. In other embodiments, retrieval bag and/or memory wire 90 might be dropped into the patient cavity 1000 and retrieved separately from the deployment system 1000.

Embodiments may lack a withdrawal string 80, or withdrawal of the actuator 300 and/or memory wire 90 may completely decouple the retrieval bag 10 from the deployment instrument 100 (actuator 300 and introducer 200) requiring the surgeon to separately retrieve the retrieval bag 10 after withdrawal of the deployment instrument.

Any retrieval bag 10 described herein may be employed with the described deployment instrument embodiments, which may or may not include tunnels. In some embodiments, memory wire 90 is coupled to the retrieval bag 10 in a first compressed position within the lumen of the introducer 200 and therefore deployed simultaneously with the retrieval bag 10. However, in other embodiments memory wire 90 may be positioned proximal to the retrieval bag 10 in the first compressed position and deployed into the retrieval bag 10 after the retrieval bag 10 is deployed from the introducer 200.

In the embodiments described herein of retrieval bag 10, memory wire 90 may be substituted by tunnels 60, wherein tunnels 60 are configured for receiving liquid or gas. This embodiment also enables expansion of the retrieval bag 10 to a predetermined shape without use of memory wire. In such embodiments, one or more tunnels are coupled to the retrieval bag and configured to expand upon injection of a fluid or gas and compress upon withdrawal of fluid or gas. Responsive to the one or more tunnels expanding, the retrieval bag expands; and wherein responsive to the one or more tunnels collapsing, the retrieval bag collapses. Retrieval bag 10 may be coupled to a luer lock to retain or release fluid within tunnels 60.

The possible configurations of the fluid tunnels 60 relative to the retrieval bag 10 are the same as the previously described possible configurations of memory wire to the retrieval bag 10, as illustrated in FIG. 1-4.

For example, in an embodiment similar to FIGS. 5 & 6 wherein the deployment instrument is an actuator 300 and introducer 200, the actuator's longitudinal body may be lumen with a hollow inner channel 303 in fluid communication with tunnels 60. Actuator 300 may have a fluid intake port 350 at its proximal end 301. The intake port 350 may be a luer lock. Upon delivery of fluid into the actuator's intake port 350, fluid travels through hollow inner channel 303 and into tunnels 60 of retrieval bag 10. Thus, instead of delivering memory wire 90 into a retrieval bag 10, the actuator may deliver fluid into one or more tunnels configured for inflation.

Delivery of fluid may be accomplished by attaching a syringe with fluid or gas to the actuator's intake port 350 and pushing the syringe piston towards the syringe's distal end. Fluid may be withdrawn from the tunnels by pulling the syringe piston towards the syringe's proximal end. Delivery rod 400 may be employed to facilitate pushing the fluid through the actuator's hollow inner channel 303, in addition or in lieu of a syringe In another embodiment similar to FIGS. 7 & 8 wherein the deployment instrument is a delivery rod 400, actuator 300, and introducer 200, delivery rod 400 may be lumen with a hollow inner channel 405 in fluid communication with tunnels 60. Delivery rod 400 may have a fluid intake port 450 at its proximal end 401. The intake port 450 may be a luer lock. Upon delivery of fluid into the delivery rod's intake port 450, fluid travels through hollow inner channel 405 and into tunnels 60 of retrieval bag 10. Thus, instead of delivering memory wire 90 into a retrieval bag 10, delivery rod 400 may deliver fluid into one or more tunnels 60 configured for inflation.

Delivery of fluid may be accomplished by attaching a syringe with fluid or gas to the delivery rod's intake port 450 and pushing the syringe piston towards the syringe's distal end. Fluid may be withdrawn from the tunnels by pulling the syringe piston towards the syringe's proximal end.

These fluid tunnel embodiments may be preferred in patients where memory wire 90 risks perforating retrieval bag 10 or the patients, or wherein memory 90 has associated high costs of manufacturing.

These fluid tunnel embodiments may include any features previously described for memory wire embodiments, including flexible arms 50, channel 70, string 80 and the relative order of steps depending on the deployment instrument utilized.

The following method 2000 illustrated a method for deploying memory wire to expand and open a retrieval bag. The operations of method 2000 presented below are intended to be illustrative. In some embodiments, method 2000 may be accomplished with one or more additional operations not described, and/or without one or more of the operations discussed. Additionally, the order in which the operations described below is not intended to be limiting.

At operation 2010, memory wire and a retrieval bag may be positioned within a deployment instrument.

At operation 2020, the retrieval bag and the memory wire may travel in a direction from a proximal end of the deployment instrument towards the distal end of the deployment instrument, and exit the distal end of the deployment instrument. While the memory wire is within the deployment instrument, the deployment instrument may apply compressive forces against the memory wire to retain the memory wire in the compressed state.

At operation 2030, responsive to the retrieval bag and the memory wire exiting the distal end of the deployment instrument, the memory wire may expand due to the compressive forces of the deployment instrument no longer being applied to the memory wire. This may also cause the retrieval bag to correspondingly expand.

At operation 2040, a surgeon may place a specimen within the expanded retrieval bag.

At operation 2050, a surgeon may retract the memory wire from the retrieval bag through the deployment instrument.

At operation 2060, a surgeon may close the drawstring of retrieval bag.

At operation 2070, a surgeon may remove the deployment instrument, holding the drawstring outside of the patient.

At operation 2080, a surgeon may pull the drawstring to remove the retrieval bag housing the specimen.

The following method 3000 illustrated a method for deploying memory wire to expand and open a retrieval bag. The operations of method 3000 presented below are intended to be illustrative. In some embodiments, method 3000 may be accomplished with one or more additional operations not described, and/or without one or more of the operations discussed. Additionally, the order in which the operations described below is not intended to be limiting.

At operation 3010, memory wire and a retrieval bag may be positioned at the distal end of an introducer.

At operation 3020, application of a compressive force to the actuator may push the retrieval bag and the memory wire distal to the introducer's distal end.

At operation 3030, responsive to the retrieval bag and the memory wire exiting the introducer, the memory wire may expand due to the compressive forces of the deployment instrument no longer being applied to the memory wire. This may also cause the retrieval bag to correspondingly expand.

At operation 3040, a surgeon may place a specimen within the expanded retrieval bag.

At operation 3050, a surgeon may retract the memory wire from the retrieval bag by pulling or applying a tensile force to the actuator.

At operation 3060, a surgeon may close the drawstring of retrieval bag.

At operation 3070, a surgeon may remove the introducer and actuator, holding the drawstring outside of the patient.

At operation 3080, a surgeon may pull the drawstring to remove the retrieval bag housing the specimen.

The following method 4000 illustrated a method for deploying memory wire to expand and open a retrieval bag. The operations of method 4000 presented below are intended to be illustrative. In some embodiments, method 4000 may be accomplished with one or more additional operations not described, and/or without one or more of the operations discussed. Additionally, the order in which the operations described below is not intended to be limiting.

At operation 4010, the actuator's distal end is proximal to introducer's distal end, the retrieval bag is positioned at the distal end of an introducer, and the memory wire is positioned at the distal end of the actuator.

At operation 4020, application of a compressive force to the actuator may push the retrieval bag distal to the introducer's distal end.

At operation 4030, application of a compressive force to the delivery rod housed within the inner channel of the actuator may push the memory wire into the retrieval bag.

At operation 4040, responsive to the retrieval bag and the memory wire exiting the introducer, the memory wire may expand due to the compressive forces of the deployment instrument no longer being applied to the memory wire. This may also cause the retrieval bag to correspondingly expand.

At operation 4050, a surgeon may place a specimen within the expanded retrieval bag.

At operation 4060, a surgeon may retract the memory wire from the retrieval bag by pulling or applying a tensile force to the delivery rod.

At operation 4070, a surgeon may close the drawstring of retrieval bag.

At operation 4080, a surgeon may remove the introducer and actuator, holding the drawstring outside of the patient.

At operation 4090, a surgeon may pull the drawstring to remove the retrieval bag housing the specimen.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Reference throughout this specification to "an embodiment", "an embodiment", "one example" or "an example" means that a particular feature, structure or characteristic described in connection with the embodiment or example is included in at least an embodiment of the present invention. Thus, appearances of the phrases "in an embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

The invention claimed is:

1. A surgical device for removal of biological specimens from within a patient, the device comprising:
    a retrieval bag having an open end, a closed end, and at least one wall extending between the open end and the closed end, wherein the open end includes a channel around the circumference to receive a string or cord with a first free end and a second free end configured to cinch or close the retrieval bag upon application of a pull or tensile force;
    flexible arms configured to be deployed to open the open end of the retrieval bag;
    one or more memory wires configured for coupling to the retrieval bag wherein the one or more memory wires are configured to collapse into a first compressed shape when receiving a compressive force, and expand into a second resting shape when the compressive force is released; wherein responsive to the one or more memory wires expanding, the retrieval bag expands; and wherein responsive to the one or more memory wires collapsing, the retrieval bag collapses, wherein the one or more memory wires extend longitudinally and radially around a sidewall of the retrieval bag in a direction from the open end towards the closed end, wherein the one or more memory wires are positioned within a hollow chamber of an actuator when the flexible arms are being deployed, wherein a proximal end of the retrieval bag is positioned more proximate to an outlet of the actuator than a distal end of the one or more memory wires when the retrieval bag and the one or more memory wires are positioned within the hollow chamber of the actuator;
    one or more tunnels coupled to the retrieval bag, the one or more tunnel being configured to receive the one or more memory wires after the retrieval bag is deployed; and wherein the one or more memory wires are configured to enter or exit the one or more tunnels.

2. The surgical device of claim 1, wherein the one or more memory wires have a smaller diameter distal end and a larger diameter proximal end;
    wherein the smaller diameter distal end is positioned closer to the retrieval bag's closed end and the larger diameter is positioned closer to the retrieval bag's open end.

3. The surgical device of claim 2 wherein the one or more memory wires are positioned on the sidewall of the retrieval bag between the open end and the closed end.

4. The surgical device of claim 1, wherein a first memory wire travels longitudinally and clockwise radially around a sidewall of the retrieval bag between the open end and the closed end; and a second memory wire travels longitudinally and counter-clockwise radially around a sidewall of the retrieval bag between the open end and the closed end.

5. The surgical device of claim 4 wherein the first memory wire and the second memory wire cross between the open end and the closed end.

6. The surgical device of claim 1, further including:
    an introducer comprised of a longitudinally extending first lumen with a first proximal end and a first distal end with a first diameter; and
    the actuator includes a longitudinal body having a second diameter smaller than the first diameter, a second proximal end and the outlet;
    wherein the actuator is positioned within the introducer and movable longitudinally through the lumen of the introducer;
    wherein the retrieval bag is positioned in a first compressed position within the lumen of the introducer and distal to the distal end of the actuator;
    wherein upon application of a first push or compressive force upon the actuator from the actuator's second proximal end and towards the outlet, the retrieval bag is moved from the first compressed position within the lumen of the introducer to a second deployed position outside of the introducer.

7. The surgical device of claim 6, wherein when the one or more memory wires are coupled to the retrieval bag in a first compressed position within the lumen of the introducer and released simultaneously with the retrieval bag in the second position when deployed outside of the introducer.

8. The surgical device of claim 6, wherein the one or more memory wires are positioned proximal to the retrieval bag in the first compressed position and deployed after the retrieval bag.

9. The surgical device of claim 8, wherein upon application of a retractive pull or tensile force to the actuator, the actuator is withdrawn from the introducer's first distal end towards the introducer's first proximal end.

10. The surgical device of claim 9, wherein the one or more memory wires remain coupled to the retrieval bag.

11. The surgical device of claim 9, wherein the one or more memory wires are withdrawn or decoupled from the retrieval bag and retracts with the actuator.

12. The surgical device of claim 11, wherein the retrieval bag is decoupled from the actuator.

13. The surgical device of claim 12, wherein the actuator's longitudinal body is a lumen with a hollow inner channel.

* * * * *